(12) United States Patent
James et al.

(10) Patent No.: US 6,228,401 B1
(45) Date of Patent: May 8, 2001

(54) PROCESSES FOR PREPARING FLUTAMIDE COMPOUNDS AND COMPOUNDS PREPARED BY SUCH PROCESSES

(76) Inventors: Jack Lawrence James, 2020 Metts Ave., Wilmington, NC (US) 28403; Louis Frank Molnar, Jr., 510 Reynolds Dr., Charlotte, NC (US) 28209; Tania E. Toney-Parker, 846 Cherry Tree Rd., Winnabow, NC (US) 28479

( * ) Notice: Subject to any disclaimer, the term of this patent is extended or adjusted under 35 U.S.C. 154(b) by 0 days.

(21) Appl. No.: 09/685,443

(22) Filed: Oct. 11, 2000

Related U.S. Application Data

(62) Division of application No. 09/059,755, filed on Apr. 14, 1998.

(51) Int. Cl.⁷ .............................. A61K 9/14; C07C 251/00
(52) U.S. Cl. ............................................ 424/489; 562/801
(58) Field of Search .................................... 424/489, 78.3, 424/1.65; 514/624; 562/802

(56) References Cited

U.S. PATENT DOCUMENTS 3,995,060 * 11/1976 Neri et al. ............................ 514/624

\* cited by examiner

*Primary Examiner*—Thurman K. Page
*Assistant Examiner*—Blessing Fubara
(74) *Attorney, Agent, or Firm*—Myers Bigel Sibley & Sajovec, P.A.; Steven A. Fontana

(57) ABSTRACT

The present invention provides processes for preparing compounds comprising flutamide API having a specific surface area of at least 0.35 $m^2/cm^3$ which comprise blending pharmaceutically acceptable diluents with unmilled flutamide API and milling the blended material until the specific surface area is at least 0.35 $m^2/cm^3$. The present invention also provides compounds prepared by such processes.

7 Claims, No Drawings

PROCESSES FOR PREPARING FLUTAMIDE COMPOUNDS AND COMPOUNDS PREPARED BY SUCH PROCESSES

CROSS-REFERENCE TO RELATED APPLICATIONS

The instant application is a divisional application of Ser. No. 09/059,755 filed Apr. 14, 1998, allowed, the disclosure of which is incorporated herein by reference in its entirety.

The present invention relates to the preparation of flutamide for incorporation into dosage forms for administration to male mammals, particularly humans, in need of treatment. The USAN name "flutamide" has been accepted for the compound having the chemical name 2-methyl-N-[4-nitro-3-(trifluoromethyl)phenyl]propanamide or 4'-nitro-3'-trifluoromethylisobutyranilide. The preparation of flutamide is disclosed in U.S. Pat. No. 3,995,060, the disclosure of which is hereby incorporated herein by reference. Flutamide is a nonsteroidal compound devoid of androgenic, adrenocortical, anti-estrogenic, estrogenic, progestational, and antifertility actions.

Flutamide has been demonstrated to be a potent antiandrogen. More particularly, U.S. Pat. No 4,329,364 discloses that flutamide is useful in treating, alleviating, and palliation of androgen-caused and/or androgen-dependent conditions such as prostatic hyperplasia including, for example, benign prostatic hypertrophy and prostatic carcinoma. In addition, U.S. Pat. No. 4,474,813 discloses conventional pharmaceutical preparations of flutamide adapted for systemic administration providing a therapeutic effect against prostatic carcinoma.

The United States Food and Drug Administration-approved therapeutic dose for flutamide is 750 mg/day in three divided doses of 250 mg/dose. The approved product, Eulexin® (Schering Corporation, Kenilworth, N.J.), is available in capsules containing 125 mg of flutamide.

However, flutamide is relatively insoluble and the approach taken to ensure adequate bioavailability and optimize the intended therapeutic benefit must be innovative. The aforementioned U.S. Pat. No. 3,995,060 mentions a standard formulation for flutamide in specific dosage units, including traditional blending, milling, and filling using traditional excipients. The '060 patent, in column 17, in a footnote, also mentions that the flutamide used in one formulation was, without more, milled post granulation so that the resulting particle size was from 5–240$\mu$. Of course, if milling of flutamide prior to formulating dosage units was known to be critical, the specifics of milling process, in addition to more specific range of critical particle sizes, including surface area, would likely have been described.

It has been discovered that the specific surface area of flutamide used in formulating final dosage forms is critical, and that the particle size range stated in the '060 patent will not provide adequate bioavailability of flutamide. In fact, it has been discovered that the particle size and specific surface area/volume ($m^2/cm^3$) of flutamide must meet specific criteria to ensure adequate bioavailability of formulated flutamide.

Accordingly, one of the objects of the present invention was to discover and define the impact particle size of flutamide active pharmaceutical ingredient has on the bioavailability of flutamide and, more particularly, flutamide's active metabolite 2-hydroxyflutamide. Through significant research, including three series of clinical trials in normal, healthy adult males,-a particle size range and range of specific surface area which provide an optimal range of flutamide blood levels in such healthy subjects, in comparison to the innovator product, Eulexin®, has been discovered. As used herein, the term "flutamide active pharmaceutical ingredient" (or flutamide API) means flutamide, or a pharmaceutically-acceptable salt thereof, without any excipients; either preformulation of after all excipients have been fully dissolved leaving only flutamide as a drug substance.

Thus, one aspect of the present invention is flutamide, as an active pharmaceutical ingredient, having a specific surface area of at least about 0.35 $m^2/cm^3$ (preferably at least 0.45 $m^2/cm^3$) and, preferably, in a range from about 0.40 $m^2/cm^3$ to about 2.50 $m^2/cm^3$. An especially preferred range is from about 0.45 $m^2/cm^3$ to about 1.50 $m^2/cm^3$, as calculated using a Sympatec laser light scattering device (Sympatec, Inc. Princeton, N.J.).

It has further been discovered that the range of particle sizes contained in any sample can also influence the bioavailability and, thus, the therapeutic benefit, from the administration of formulated flutamide API. As such, another aspect of the present invention is flutamide, as an active pharmaceutical ingredient, in which fifty percent (50%) of the particles of each sample ($X_{50}$) is less than 26.0$\mu$, preferably in the range from about 5.0$\mu$ to about 20.0$\mu$. Furthermore, the present invention also provides flutamide, as an active pharmaceutical ingredient, in which ninety percent (90%) of the particles in each sample ($X_{90}$) is less than 130.0$\mu$, preferably from about 10.0$\mu$ to about 130.0$\mu$, and especially from about 15.0$\mu$ to about 60.0$\mu$.

Flutamide active pharmaceutical ingredient, having the specific surface area and/or the $X_{50}$ and/or $X_{90}$ values as set forth herein above, is prepared through milling techniques generally well known to one of ordinary skill in the art, without causing chemical and/or heat degradation of flutamide API. Typically, a jet mill, pin disc mill, ball mill, hammer mill, oscillating mill, roller mill, chaser mill, rotary cutters, collared mill, fluid energy mill, and the like may be used. Preferably, a jet mill is used to provide the desired specific surface area of at least about 0.35 $m^2/cm^3$, but each type of mill could give the desired results by varying the speed of the mill, the amount of flutamide API fed into the mill, and/or the grinding period. In all cases, it is also possible to obtain product with the desired specific surface area by mixing flutamide API of different specific surface areas.

Because unmilled flutamide has a consistency which readily agglomerates rendering milling difficult with inconsistent results, it was also discovered that flutamide API is best milled when combined with one or more pharmaceutically acceptable diluents including, for example, a starch such as corn starch, and the like, sugars such as lactose and mannitol, and the like, cellulose derivatives such as microcrystalline cellulose, and the like, inorganic salts such as dibasic calcium and phosphate dihydrate, and the like. Of these, lactose is especially preferred. The addition of such a diluent prevents agglomeration of flutamide API and improves the flow characteristics of flutamide API, thus aiding in accurately preparing the desired specific surface area and $X_{50}$ and $X_{90}$ particle size values. The addition of such diluents is accomplished using standard blending techniques which are well know in the art. It was further discovered that a ratio of diluent to flutamide API of about 4:1 to about 1:1 would facilitate the milling of flutamide API, while a ratio of about 2:1, particularly when the diluent was lactose, optimized the milling of flutamide API to the desired surface area and particle size parameters. When lactose was used at this ratio, the appropriate amounts of flutamide API and lactose are present for the next step in formulating flutamide to a final dosage form suitable for administration to a patient in need of treatment.

Accordingly, the present invention also provides a method of preparing flutamide API wherein the specific surface area of such flutamide API is at least 0.35 $m^2/cm^3$, preferably from about 0.40 $m^2/cm^3$ to about 2.50 $m^2/cm^3$, and especially from about 0.45 $m^2/cm^3$ to about 1.50 $m^2/cm^3$, and/or the particle $X_{50}$ size value is less than about 26.0$\mu$, preferably from about 5.0$\mu$ to about 20.0$\mu$, and/or the $X_{90}$ particle size value is less than 130.0$\mu$, preferably from about 10.0$\mu$ to about 130$\mu$, especially from about 15.0$\mu$ to about 60.0$\mu$, comprising blending said flutamide API with a pharmaceutically acceptable diluent, preferably lactose, at a ratio of diluent to flutamide API from about 4:1 to about 1:1, preferably about 2:1, and milling the blended composition of diluent and flutamide API to the desired specific surface area and/or the desired $X_{50}$ and/or $X_{90}$ particle size.

A further aspect of the present invention is flutamide API having the above-specified specific surface area and/or $X_{50}$ and/or $X_{90}$ particle size values when milled, generally and, particularly, when prepared by the above-described process.

The present invention further relates to a pharmaceutical composition in a unit dosage form, useful in the treatment of prostatic carcinoma, comprising a therapeutically effective amount of flutamide API, or a pharmaceutically acceptable salt thereof, such flutamide having the specific surface area of the present invention as set forth herein above, and/or the $X_{50}$ and/or $X_{90}$ particle size values of the present invention as set forth herein above, together with at least one pharmaceutically acceptable excipient, diluent, or carrier.

Numerous studies have shown flutamide to be useful in the treatment of prostatic carcinoma. The compositions of the present invention are useful for the treatment of such carcinoma, in addition to the treatment of other androgen dependent carcinomas.

It will be understood by the prescribing clinician that carcinomas are complex and difficult conditions to treat, and that no single treatment will necessarily be effective in curing a particular patient. However, in view of the severity of the condition involved, the relative absence of serious side effects for effective dosages of flutamide, and the possibility of achieving at least an ameliorative effect, the compositions of the present invention are useful in this context.

In the treatment of prostatic carcinoma, the compositions of the present invention should provide a quantity of flutamide API equivalent to a dose of about 2 to about 30 mg/kg of patient body weight per day, preferably about 4 to about 20 mg/kg of body weight per day, and more preferably about 7 to about 14 mg/kg of body weight per day. The aforementioned doses may be divided into two or more portions for administration over the course of the day, for example, one-third of the daily dose administered three times per day. Pharmaceutical preparations for a 70 kg mammal should provide a daily dose of flutamide API, or a pharmaceutically acceptable salt thereof, of about 100 mg to about 2000 mg, preferably about 250 mg to about 1500 mg, and more preferably about 500 mg to about 1000 mg, and should be continued until symptomatic relief is obtained, as ascertained by the attending diagnostician.

Pharmaceutical compositions of the present invention can be prepared by procedures known in the art. For example, the compounds can be formulated with common excipients, diluents, or carriers, and formed into tablets, capsules (e.g. hard or soft gelatin capsules), suspensions, powders, and the like. Examples of pharmaceutically acceptable excipients, diluents, and carriers that are suitable for such compositions include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such a corn starch calcium carbonate and sodium bicarbonate; agents for retarding dissolution such as paraffin; resorption accelerators such as quaternary ammonium compounds; surface active agents such as sodium lauryl sulfate (SLS), cetyl alcohol, and glycerol monostearate; adsorptive carriers such as kaolin and bentonite; and lubricants such as talc, calcium and magnesium stearate, and polyethylene glycols.

The present compositions also include elixirs or oral solutions for convenient oral administration or as solutions appropriate for parenteral administration, for example, in ampules or vials for intramuscular, subcutaneous, or intravenous routes. Additionally, the compounds are well suited to compositions as sustained release dosage forms, and the like. The compositions can be so constituted that they release the active ingredients only or, preferably, in a particular physiological location, possibly over a period of time. The coatings, envelopes, and protective matricies may be made, for example, from polymeric substances or waxes.

Additionally, the present compositions may be in the form of suppositories (both rectal and urethral). In oral dosage form, the excipients, diluents, or carriers may include a standard, pharmaceutically acceptable, natural or synthetic flavoring agent.

Preferably, the aforementioned compositions are so proportioned as to afford a unit dosage of about 125 mg to about 250 mg of flutamide API. Thus, for example, a preferred dosage of 750 mg per day could be administered as one 250 mg tablet or capsule three times per day, or two 125 mg tablets or capsules three times per day.

It has also been discovered that the administration of flutamide compositions of the present invention to healthy, human male subjects results in blood levels of the primary, highly active metabolite of flutamide, 2-hydroxyflutamide, consistent with blood levels provided by the innovator product, Eulexin®. It was further discovered that similar compositions, but having specific surface areas of flutamide API less than the limits set forth herein for the present invention, as well as $X_{50}$ and $X_{90}$ particle size values which were greater than the limits set forth herein for the present invention, failed to provide 2-hydroxyflutamide blood levels in such male subjects which were consistent with blood levels provided by the innovator product, Eulexin® based on a 90% confidence interval for which a geometric mean ratio of area (area under the curve) to $C_{max}$ (maximum blood level concentration) which falls within a range of 0.80 to 1.25 comparing a formulation of the present invention to Eulexin®.

These results demonstrate that each aspect of the present invention represents a novel, significant advancement in the art for the therapeutic treatment of prostatic carcinoma. Accordingly, the present invention further provides flutamide API having a specific surface area of at least 0.35 $m^2/cm^3$, preferably having a specific surface area of from about 0.40 $m^2/cm^3$ to about 2.50 $m^2/cm^3{}_1$, and more preferably from about 0.45 $m^2/cm^3$ to about 1.50 $m^2/cm^3$; and/or an $X_{50}$ particle size value less than 26.0$\mu$, preferably in the range from about 5.0$\mu$ to about 20.0$\mu$, and/or an $X_{90}$ particle size value of less than 130.0$\mu$, preferably in the range from about 10.0$\mu$ to about 130.0$\mu$, and more preferably in the range from about 15.0μ to about 60.0μ and further having a 90% confidence interval for which the 2-hydroxyflutamide of said flutamide API geometric mean area and peak concentration ratio is within the interval 0.80–1.25 when comparing equal doses of such flutamide API and Eulexin®. One of ordinary skill in the art will readily appreciate that such geometric mean ratio is calculated based on the 2-hydroxyflutamide blood level analysis of samples extracted from healthy, male, human subjects, preferably following an overnight fast, following the administration of equal doses, at equivalent timing, of Eulexin®. The calculation of geometric mean ratios, and the significance of the 0.80 to 1.25 range at the 90% confidence level, are also well known to one of ordinary skill in the art.

Based on the discovery that compositions of the present invention provide geometric mean ratios of the 2-hydroxyflutamide metabolite which are equivalent to Eulexin®, and that the 2-hydroxyflutamide metabolite (converted in vivo from what has been characterized as a prodrug, flutamide) is highly active against mammalian prostatic carcinoma and other androgen dependent carcinomas [see, e.g., Katchen, B., et al., *J Clin Endocrinal Metab*, 41:373–379 (1975); Radwanski, E., et al., *J Clin Pharmocol*, 29:554–558 (1989); Brogden, R. N., et al., *Drugs*, 38:185–203 (1989); and Simard, J., et al., *Molecular and Cellular Endocrinology*, 44:261–270 (1986)]. The present invention provides a method of providing a therapeutic effect against androgen dependent carcinomas, particularly prostatic carcinomas, comprising administering to a male mammal, particularly a human, in need of treatment a therapeutically effective amount of a composition of the present invention.

In addition, the combination treatment of flutamide and a peptide of the formula $^P$Glu-His-Trp-Ser-Tyr-X-Y-Arg-Pro-Z  (Formula I)

wherein a) Z is Gly-NH$_2$, Y is Leu and X is Gly;
b) Z is Gly-NH$^2$, Y is Leu, X is DN Leu, DN Val, D abu (α-aminobutyric acid), D Phe, D Ser, D Thr, D Met, D Pgl, D Lys, Leu Ile, Nle, Val, N Val, Met, Phe, D Leu, D Arg, D Ser (tbu), D Thr (tbu), D Cys (tbu), D Asp (Otbu), D Gly (Otbu), D Orn (boc), D Lys (boc), D Trp, Trp, 2methyl Ala, D Tyr, D Met, ε-lauryl-D Lys, ε-dextran-D Lys;
c) Z is NH-cyclopropyl or —NH-Alk wherein Alk is alkyl of 1 to 3 carbon atoms, Y is Leu and X is D Ser (tbu), D Thr (tbu), D Asp (Otbu), D Glu (Otbu), D Orn (boc), D Lys (boc);
d) Z is —NH—CH$_3$, —NH—CH$_2$—CH$_3$, —NH—CH$_2$—CH$_2$CH$_3$, —NH—CH$_2$—CH$_2$—OH,

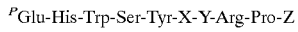

Y is Leu and X is Gly;
e) Z is NH—CH$_2$—CH$_3$, Y is Leu and X is D Trp, D Leu, D Ala, D Ser (tbu), D Tyr, D Lys, Ala;
f) Z is Gly-NH$_2$, or —NH—CH$_2$—CH$_3$, Y is Nαα Me Leu and X is Gly;
g) Z is —NH-cyclopropyl, Y is Leu and X is D Leu; or
h) Z is Gly-NH$_2$, —NH-cyclopropyl or —NHAlk' wherein Alk' is alkyl of 1 to 3 carbon atoms, Y is Ser (but), Cys (but), Asp (Obut), Glu (Obut), Orn (boc), Lys (bos) and X is Gly, or a pharmaceutically acceptable salt thereof.

is known to the art to have a therapeutic benefit for the treatment of prostate adenocarcinoma and prostate benign hypertrophia [see, e.g., U.S. Pat. No. 4,472,382, the disclosure of which is hereby incorporated herein by reference]. Accordingly, the administration of a therapeutically effective amount of a composition of the present invention in association with an effective amount of a peptide of Formula I, particularly when such Formula I peptide is [D Ser (Tbu)$^6$, of Des Gly NH$_2$$^{10}$] LH-RH ethylamide, or, D Ser (Tbu)$^6$ or Gly$^{10}$ LH-RH ethylamide, or generally, an agonist of LH-RH as taught in U.S. Pat. No. 5,712,251 (which is herein incorporated by reference) which is a division of above-referenced U.S. Pat. No. 4,472,382, are useful for providing a therapeutic effect against prostate adenocarcinoma and benign prostate hypertrophy in a male mammal, particularly a human, in need of treatment. Thus, another aspect of the present invention provides a method for providing such a therapeutic effect against prostate adenocarcinoma and benign prostate hypertrophy.

Methods of administering, dose regimen, and preferred dosages of flutamide are as set forth herein, and preparation, methods of administering, dose regimen, and preferred dosages of peptides of Formula I are as set forth in above-referenced U.S. Pat. Nos. 4,472,382 and 5,712,251. Preparation of pharmaceutically acceptable salts of such peptides are well known to the ordinarily skilled artisan.

The following examples are illustrative and describe several preferred embodiments of the present invention. However, such embodiments are not intended to limit the scope of the present invention.

EXAMPLE 1

Milling of Lot 03—Single Pass

A 1.0 cubic foot Gemco (Middlesex, N.J.) blender was charged with 7329 g of lactose which was previously hand screened through a 20 mesh stainless steel screen, and 3300 g of flutamide API. The substances were blended for 125 revolutions. After setting the air pressure of the feed side inlet jet of a Trost TX jet mill (Garlock, Inc., Newtown, Pa.) at 70 psi and the opposing jet at 65 psi, the blend was fed into the mill at 75–100 g/minute.

EXAMPLE 2

Milling of Lot 04—Triple Pass

The process set forth in Example 1 was used except the pressure for the jets were set at 85 psi and 80 psi, respectively, and the material passed through the mill three times.

EXAMPLE 3

Milling of Lot 05—Single Pass

For each of four sublots, a 1.0 cubic foot Gemco blender was charged with 9,772 g of lactose (including a 10% excess) after the lactose was passed through a 20 mesh stainless steel screen in a Stokes oscillating granulator (Stokes Vacuum, Inc., Philadelphia, Pa.), and 4,400 g of flutamide API. The substance was blended for 125 revolutions. After setting the air pressure of the feed side inlet jet of the Trost TX jet mill at about 70–82 psi and the opposing jet at 65–77 psi with a differential of about 5 psi between the two sides, the blended material was fed into the jet mill at a rate of 75–100 g/minute via a vibrating trough.

EXAMPLE 4

Milling of Lot 06—Triple Pass

The process set forth in Example 3 was used except the pressure for the jets were set at 80–85 psi and 70–75 psi, respectively, and the material was passed through the mill three times, and the feed rate was 20–25 g/minute.

EXAMPLE 5

Particle Size and Specific Surface Area

The following procedure was used to determine the $X_{50}$ and $X_{90}$ values for particle size and the specific surface area for the above Examples:

A saturated media was prepared by placing an excess of milled flutamide API in a solution comprising Milli-Q water and 0.1% soldium lauryl sulfate (SLS) and stiring at ambient temperature for 1 hour. The resulting media was filtered using a PTFE filter to remove excess undissolved flutamide API. A base line reference was established by adding 100 mL of the saturated media to a suspension cell of a Sympatec lazer light scattering device. Determination of particle size values for individual samples was achieved by slowly adding aliquots of the desired sample to the suspension cell until an optical concentration of about 10% was achieved. Particle size was determined at 4, 8, and 18 minutes after addition. Results for the $X_{50}$ and $X_{90}$ particle size for flutamide API, prior to formulation for administration to subjects in clinical trials are as follows:

| Flutamide Particle Size Values and Specific Surface Area | | | | |
|---|---|---|---|---|
| Example Number | Time to Sample (minutes) | $X_{50}$ | $X_{90}$ | Specific Surface Area ($m^2/cm^3$) |
| 1 | 4 | 17.65 | 47.03 | 0.51 |
|   | 8 | 17.62 | 45.37 | 0.51 |
|   | 18 | 17.66 | 46.34 | 0.51 |
| 2 | 4 | 7.40 | 18.83 | 1.50 |
|   | 18 | 7.43 | 18.95 | 1.50 |
|   | 18 | 7.41 | 18.86 | 1.50 |
| 3 | 4 | 20.99 | 54.24 | 0.47 |
|   | 8 | 20.97 | 54.52 | 0.47 |
|   | 18 | 20.90 | 53.86 | 0.47 |
| 4 | 4 | 7.86 | 21.24 | 1.46 |
|   | 8 | 7.87 | 21.54 | 1.46 |
|   | 18 | 8.83 | 21.02 | 1.47 |

Using standard techniques, the following flutamide composition was prepared using milled samples 1–4 using a wet granulation method:

EXAMPLE 6

| Capsule Formulation | |
|---|---|
| Ingredients | Milligrams per Capsule |
| Flutamide API[a] | 125.0 |
| Lactose, monohydrate[a] | 277.6 |
| Sodium lauryl sulfate[a] | 12.0 |
| Povidone, USP[a] (Polyvinylpyrrolidone) | 20.8 |

| Capsule Formulation | |
|---|---|
| Ingredients | Milligrams per Capsule |
| Corn Starch, NF[b] | 64.2 |
| Magnesium Stearate, NF | 0.4 |
| Water, USP[c] | 116.5 |
| Capsule weight | 500.0 mg |

[a]10% excess is required for manufacturing.
[b]Corn starch is adjusted for water content, typically about 10% by weight.
[c]Water is used as a granulation agent and is added and then dried with no net addition.

Addition compositions are prepared using milled samples from Examples 1–4:

EXAMPLE 7

| Tablet Formulation | |
|---|---|
| Ingredients | Milligrams per Tablet |
| Flutamide API | 250.00 |
| Lactose, anhydrous | 221.70 |
| Sodium lauryl sulfate | 15.00 |
| Microcrystalline cellulose | 100.00 |
| Starch | 162.50 |
| Water (evaporates) | (0.29) |
| Silica gel (Syloid 244) | 0.40 |
| Magnesium Stearate | 0.40 |
| Tablet weight | 750.00 mg |

Blend the above ingredients using a wet granulation method and compress into tablets using standard techniques.

EXAMPLE 8

| Parenteral Suspension Formulation | |
|---|---|
| Ingredients | Milligrams per Milliliter |
| Flutamide API | 250.00 |
| Methyl cellulose 15 cps., USP | 0.25 |
| Sodium citrate, dihydrate | 30.00 |
| Benzyl alcohol, NF | 9.00 |
| Methylparaben, USP | 1.80 |
| Propylparaben, USP | 1.20 |
| Water for injection, USP q.s.a.d. | 1.00 |

Using standard techniques, combine the above ingredients to prepare a parenteral suspension.

EXAMPLE 9

| Capsule Formulation | | | |
|---|---|---|---|
| Ingredients | Milligrams per Capsule | | |
| Flutamide | 125.0 | 250.0 | 200.0 |
| Lactose, hydrous, USP | 360.5 | 221.7 | 185.0 |
| Sodium lauryl sulfate, NF | 12.0 | 12.0 | 12.0 |
| Povidone, USP (Polyvinylpyrrolidone) | 25.0 | 25.0 | 25.0 |
|  | 162.5 |  |  |
| Water, purified, USP (evaporated) or | — | — | — |
| S.D. alcohol, 3-A (evaporated*) | — | — | — |

-continued

Capsule Formulation

| Ingredients | Milligrams per Capsule | | |
|---|---|---|---|
| Magnesium Stearate, NF | 0.5 | 0.5 | 1.0 |
| Capsule weight | 600.0 mg | 600.0 mg | 500.0 mg |

*Approximately 75 mL 3-A alcohol/100 capsules, or 60 mL water/1000 capsules. Blend the above by standard techniques and fill into capsules.

Test Procedure I

A randomized, single-dose, two-way crossover study was conducted with 30 healthy, adult volunteers (29 completed) to evaluate two flutamide formulations containing unmilled flutamide API compared to the reference product Eulexin®. A single dose of two, 125 mg flutamide capsules (total dose 250 mg) was administered after an overnight fast.

Blood samples were collected prior to each dose and at intervals over a 72 hour period. Plasma concentrations of flutamide and its active metabolite, 2-hydroxyflutamide, were measured by GC-MS analyses. Pharmacokinetic and statistical analyses were conducted to determine if the test and reference capsules are bioequivalent.

The 90% confidence interval for the test-to-reference 2-hydroxyflutamide geometric mean area and the peak concentration ratios were not within the interval 0.80–1.25.

Test Procedure II

A randomized, single-dose, two-treatment, four-period replicated crossover study was conducted with 43 healthy, adult volunteers (41 completing all four periods) to evaluate two flutamide formulations containing milled flutamide of the present invention (Examples 3 and 4) compared to the reference product, Eulexin®. A single dose of two, 125 mg flutamide capsules (total dose 250 mg) was administered in each study period after an overnight fast. There was a one-week washout between treatments.

Blood samples were collected prior to each dose and 15 times over 24 hours after each dose. Plasma concentrations of flutamide and its active metabolite, 2-hydroxyflutamide, were measured by GC-MS analysis. Pharmacokinetic and statistical analyses were conducted to determine if the test and reference capsules are bioequivalent. The 90% confidence interval for the test-to-reference 2-hydroxyflutamide geometric mean area and peak concentration ratios were within the interval 0.80–1.25.

We claim:

1. A process for preparing a compound comprising flutamide API having a specific surface area of at least 0.35 $m^2/cm^3$ comprising blending a pharmaceutically acceptable diluent with unmilled flutamide API and milling the blended material until the specific surface area is at least 0.35 $m^2/cm^3$.

2. A process according to claim 1 wherein the blending ratio of said pharmaceutically acceptable diluent and said unmilled flutamide API is from about 4:1 to about 1:1.

3. A process according to claim 2 wherein the blending ratio of said pharmaceutically acceptable diluent and said unmilled flutamide API is about 2:1.

4. A process according to claim 3 wherein said pharmaceutically acceptable diluent is lactose.

5. A process for preparing a compound of claim 1 comprising blending a pharmaceutically acceptable diluent with unmilled flutamide API and milling the blended material until the specific surface area is at least 0.35 $m^2/cm^3$, the $X_{50}$ particle size value is less than 26.0$\mu$, and the $X_{90}$ particle size value is less than 130.0$\mu$.

6. Flutamide API when prepared by a process according to claim 1.

7. Flutamide API when prepared by a process according to claim 5.

* * * * *